(12) United States Patent
Tatake et al.

(10) Patent No.: US 7,045,346 B2
(45) Date of Patent: May 16, 2006

(54) NUCLEIC ACID CONSTRUCTS USEFUL FOR GLUCOSE REGULATED PRODUCTION OF HUMAN INSULIN IN SOMATIC CELL LINES

(75) Inventors: Revati J. Tatake, Sandy Hook, CT (US); Richard Schneiderman, Sandy Hook, CT (US); Randall Wilber Barton, Farmington, CT (US)

(73) Assignee: Boehringer Ingelheim Pharmaceuticals, Inc., Ridgefleid, CT (US)

( * ) Notice: Subject to any disclaimer, the term of this patent is extended or adjusted under 35 U.S.C. 154(b) by 164 days.

(21) Appl. No.: 10/166,147

(22) Filed: Jun. 10, 2002

(65) Prior Publication Data

US 2003/0032144 A1   Feb. 13, 2003

Related U.S. Application Data

(60) Provisional application No. 60/299,334, filed on Jun. 19, 2001, provisional application No. 60/296,936, filed on Jun. 8, 2001.

(51) Int. Cl.
*C12N 15/00* (2006.01)
*C12N 15/09* (2006.01)
*C12N 15/63* (2006.01)
*C12N 15/70* (2006.01)
*C12N 15/74* (2006.01)

(52) U.S. Cl. .................................. 435/320.1; 435/325
(58) Field of Classification Search ............. 435/320.1, 435/325, 455, 456; 424/93.21
See application file for complete search history.

(56) References Cited

U.S. PATENT DOCUMENTS

| | | | |
|---|---|---|---|
| 4,992,418 A | 2/1991 | Katsoyannis | |
| 5,962,267 A | 10/1999 | Shin et al. | |
| 6,242,426 B1 | 6/2001 | Kurtzman et al. | |
| 6,274,365 B1 * | 8/2001 | van de Ven et al. | 435/219 |
| 6,537,806 B1 * | 3/2003 | Osborne et al. | 435/325 |
| 2001/0007656 A1 | 7/2001 | Bosch et al. | |

OTHER PUBLICATIONS

Barry, S. C. et al; "Glucose-Regulated Insulin Expression In Diabetic Rats"; Human Gene Therapy 12:131-139; 2001.

Debyra J. Groskreutz et al; Genetically Engineered Proinsulin Constitutively Processed and Secreted as Mature, Active Insulin; The Journal of Biological Chemistry Feb. 25, 1994 vol. 269 p. 6241-6245; The American Society for Biochemistry and Molecular Biology, Inc.

David J. Freeman et al; Present and potential future use of gene therapy for the treatment of non-insulin dependent diabetes mellitus (Review); International Journal of Molecular Medicine (1999) vol. 4 pp. 585-592; Dept. of Biochemistry School of Medical Science, Bristol, UK.

International Search Report Reference No. PCT/US02/18291.

Simon C. Barry et al; Glucose-Regulated Insulin Expression in Diabetic Rats; Human Gene Therapy Jan. 20, 2001 vol. 12 pp. 131-139; Department of Pediatrics and Department of Medicine, Seattle, WA. 98195.

* cited by examiner

*Primary Examiner*—Joseph Woitach
*Assistant Examiner*—Brian Whiteman
(74) *Attorney, Agent, or Firm*—Michael P. Morris; Mary-Ellen M. Devlin; Alan R. Stempel

(57) ABSTRACT

Unique multifunctional nucleotide expression cassettes comprising a nucleotide sequence encoding a human protease driven by a glucose-regulatable promoter, a nucleotide sequence encoding human proinsulin having sites at its B-C and C-A junctions altered to permit cleavage by the human protease, and a CMV promoter driving the transcription of the nucleotide sequence encoding the human proinsulin, such cassettes optionally having polyadenylation sequences after each structural gene and the nucleotide sequence encoding human proinsulin optionally carrying an H10D variant, and cells transformed thereby.

23 Claims, 5 Drawing Sheets

SEQUENCE LISTING

<160> NUMBER OF SEQ ID NOS: 4

<210> SEQ ID NO 1
<211> LENGTH: 37
<212> TYPE: DNA
<213> ORGANISM: human furin
<220> FEATURE:
<221> NAME/KEY: primer
<222> LOCATION: (4)..(24)
<223> OTHER INFORMATION: A forward primer containing SalI and SnaB1
      restriction sites at positions 4-9 and 10-15, respectively; and
      Kozak sequence at positions 16-24.

<400> SEQUENCE: 1
aaagtcgact acgtaccacc atggagctga ggcccttt                              37

<210> SEQ ID NO 2
<211> LENGTH: 35
<212> TYPE: DNA
<213> ORGANISM: human furin
<220> FEATURE:
<221> NAME/KEY: primer
<222> LOCATION: (4)..(15)
<223> OTHER INFORMATION: A reverse primer containing BclI and BsiWI
      restrictions sites at positions 4-9 and 10-15, respectively

<400> SEQUENCE: 2
aaatgatcac gtacgtcaga gggcgctctg gtctt                                 35

<210> SEQ ID NO 3
<211> LENGTH: 35
<212> TYPE: DNA
<213> ORGANISM: TGF-alpha promoter 1
<220> FEATURE:
<221> NAME/KEY: primer
<222> LOCATION: (4)..(15)
<223> OTHER INFORMATION: A forward primer containing ClaI and HpaI
      restriction sites at positions 4-9 and 10-15, respectively

<400> SEQUENCE: 3
aaaatcgatg ttaacagctc cgggtcactg gagaa                                 35

```
<210> SEQ ID NO 4
<211> LENGTH: 35
<212> TYPE: DNA
<213> ORGANISM: TGF-alpha promoter 2
<220> FEATURE:
<221> NAME/KEY: primer
<222> LOCATION: (4)..(15)
<223> OTHER INFORMATION: A reverse primer containing SalI and SnaBI
      restriction sites at positions 4-9 and 10-15, respectively

<400> SEQUENCE: 4
aaagtcgact acgtaggcgg agcggcgccg cggtg                              35
```

NUCLEIC ACID CONSTRUCTS USEFUL FOR GLUCOSE REGULATED PRODUCTION OF HUMAN INSULIN IN SOMATIC CELL LINES

RELATED APPLICATIONS

The present application claims priority to U.S. provisional application No. 60/296,936, filed Jun. 8, 2001 and U.S. provisional application No. 60/299,334, filed Jun. 19, 2001, the priority benefits of which are hereby claimed.

BACKGROUND OF THE INVENTION

1. Field of the Invention

The present invention relates to gene constructs useful for modifying cell lines to effectuate glucose-regulated production of human insulin, and cell lines transformed by such gene constructs.

2. Background of the Related Art

Diabetes mellitus is a chronic disorder of fat, carbohydrate, and protein metabolism. It is characterized by an under-utilization of glucose and an absolute or relative insulin deficiency. Persons suffering from the disease in full expression have a tendency to fasting hyperglycemia, glycosuria, and ultimately to the development of atherosclerosis, neuropathy, nephropathy and microangiopathy. Diabetes is the seventh leading cause of death (the sixth-leading cause of death by disease) in the United States. It is also the leading cause of new cases of blindness in persons ages 20–74 and the leading cause of end-stage renal disease (accounting for about 40% of new cases). Persons afflicted with diabetes have about 15–50 times greater risk of leg amputation, 2–4 times the risk of heart disease, and are 2–4 times more likely to suffer a stroke than the general population.

The pathology of diabetes mellitus can be attributed to three major effects of insulin insufficiency: (1) a decrease in the utilization of glucose by the body cells, causing an increase in blood glucose to supranormal levels; (2) a marked increase in the mobilization of fats from the fat storage areas, causing abnormal fat metabolism as well as the deposition of lipids in vascular walls to cause atherosclerosis and (3) depletion of protein in the tissues of the body. Diabetes is a chronic disease that presently has no cure.

Diabetes mellitus is generally classified into three major forms: type 1 insulin-dependent diabetes (IDDM), often referred to as immune-mediated diabetes; type 2 non-insulin dependent diabetes (NIDDM); and diabetes due to variants in genes controlling beta cell function or metabolism. IDDM accounts for about 10% of all cases of diabetes. Type 1-IDDM is an immune-mediated disease that is associated with a near complete loss of the pancreatic beta cells resulting in insulin dependence for life. It can occur at any age, and it is estimated that about 1% of all newborns will develop the disease during their lifetime. Type 2-NIDDM accounts for most of the remaining 90% of cases of diabetes. Type 2-NIDDM is thought to occur as a result of both external and complex genetic influences which contribute to a peripheral insulin resistance with tissues failing to utilize glucose appropriately in response to the insulin signal. Allelic variants at the insulin locus itself have been associated with NIDDM, with the variants exhibiting altered properties with regard to transcriptional regulation. A very small percentage of diabetics have their condition secondary to variants in genes controlling beta cell function or metabolism.

Glucose homeostasis involves numerous neuroendocrine systems, however, the pancreatic islets of Langerhans are considered to be the primary "glucose sensor" in mammals. Pancreatic islets are composed of primarily four different populations of cells which may be characterized by their production of insulin, glucagon, somatostatin or pancreatic polypeptide. Insulin-producing beta cells predominate in the islets. However, the islet cell mass makes up only a small fraction (approximately 1%) of the total pancreas. Early stage Type 2-IDDM and Type 1-IDDM is characterized by a progressive loss of beta-cell function. Insulin secretion from islet beta-cells is stimulated by amino acids, three carbon sugars such as glyceraldehyde, and most prominently, glucose.

Transport of glucose into the beta cell, and metabolism of glucose therein, are absolute requirements for the secretion of insulin, i.e., (glucose stimulates insulin secretion from the beta-cells of the islets of Langerhans through its own metabolism). As in normal beta-cells glucose transport capacity is in excess relative to glycolytic flux, breakdown of glucose is the true rate-limiting step.

Glucose stimulates de novo insulin biosynthesis by increasing transcription, mRNA stability, translation and protein processing. It also rapidly stimulates the release of pre-stored insulin. The human insulin gene is encoded on the short arm of chromosome 11 and contains three exons and two introns. Transcriptional control of the insulin gene is achieved through a short region of flanking DNA that interacts with cell-specific and glucose-sensitive signaling molecules. The precise nature of the regulatory organization is poorly understood. However, it is generally believed that the basic helix-loop-helix and homeodomain-containing factors are critical components of the transcriptional machinery that governs beta-cell specific expression of insulin. The primary messenger RNA transcript is processed by the removal of intervening sequences and by the addition of a poly-A tail at its 3' end to produce mature insulin messenger RNA. Translation of the m-RNA is at the rough endoplasmic reticulum yielding preproinsulin.

Preproinsulin differs from mature insulin in two ways: (1) it has a N-terminal "signal" or "pre" sequence which directs the polypeptide to the rough endoplasmic reticulum where it is proteolytically processed, and (2) contains an additional connecting peptide, known as the C-peptide, between the A and B chains, the C-peptide permitting correct folding of the whole molecule.

The signal sequence of preproinsulin is co-translationally removed in the endoplasmic reticulum to form proinsulin. Proinsulin is trafficked to the Golgi apparatus where it is subsequently transferred to regulated secretory vesicles wherein it is processed into mature insulin by proteolytic cleavage of the C-peptide.

Proinsulin processing occurs primarily in clathrin-coated immature secretory granules derived from the trans-Golgi network (TGN) of the pancreatic beta-cell. Proteolytic processing of proinsulin to insulin is by means of prohormone convertases of the subtilisin family of endoproteases. These convertases cleave peptide bonds carboxyl-terminal to dibasic residues, and in combination with carboxypeptidase E/H which removes the basic residues from the B chain, generating the mature functional insulin that is secreted into the circulation. That is, complete conversion involves endoproteolytic cleavage of the COOH-terminal to two pairs of basic residues linking the insulin B-chain to C-peptide ($Arg^{31}$-$Arg^{32}$) and C-peptide to the A-chain ($Lys^{64}$-$Arg^{65}$) as well as trimming of the remaining COOH-terminal basic residues by carboxypeptidase E/H (Davidson et al., Biochem. J. 245:

575 (1987); Grimwood et al., J. Biol. Chem. 264: 15662 (1989)). Secretory vesicles are derived from Golgi membranes by a process of budding off and eventual separation. The vesicles are transported to the plasma membrane surface of a cell in response to secretory stimuli such as glucose, where they fuse with the plasma membrane and release their stores of the mature hormone.

It has been hypothesized that glucose's specific stimulatory effect is mediated by, and proportional to, its flux rate through glycolysis and related pathways. Evidence is accumulating implicating a specific facilitated-diffusion type glucose transporter known as GLUT-2, and the glucose phosphorylating enzyme, glucokinase, in the control of glucose metabolism in islet beta-cells. Both proteins have affinities for glucose that allow large changes in activities over the physiological range of glucose.

Diabetes is treated by correcting insulin concentrations in the body in such a manner that the patient has normal or nearly normal carbohydrate, fat and protein metabolism as possible. Optimal therapy has been found to be effective at preventing most acute effects of diabetes, and to greatly delay the chronic effects as well. It is generally agreed that very little progress has been made in the clinical treatment of diabetic patients in the last twenty years.

Treatment for diabetes is still centered around self-injection of exogenous insulin once or twice daily, or in the case of non-severe diabetes wherein the islets still maintain the potential to secrete insulin, the use of drugs that stimulate insulin secretion such as the sulfonylureas. Exogenous insulin may be isolated by non-recombinant methods as from the purification of insulin from freshly isolated porcine or bovine pancreas, or by employment of recombination techniques. Recombinant methods generally include the expression of recombinant proinsulin in bacteria or yeast, followed by chemical treatment of the proinsulin to ensure correct disulfide bond linkages between the A and B chains of the mature insulin molecule. The mature insulin peptide is purified away from the bacterial or yeast proteins, as well as any added material. The bacterial recombinant procedure typically entails as many as forty distinct steps.

Treatment of diabetes conventionally also involves establishing the patient on a standard diet containing normal, well-controlled amounts of carbohydrates, and on a regular exercise program. Weight management is often useful as decreased fat reduces the insulin requirements of an individual. Exercise increases the transport of glucose into the muscle cells even in the absence of insulin, and thus actually has an insulin-like effect.

In conjunction with injections of insulin, diet, and exercise programs, the treatment of diabetes requires a constant and life-long monitoring of blood glucose. As many diabetic patients have difficulty in meeting all these strictures, they constantly expose themselves to the adverse effects of hypoglycemia and hyperglycemia. There is a need therefore for alternative methods for controlling blood glucose levels in the diabetic patient.

Numerous researchers have attempted to control insulin delivery through the use of external devices such as insulin pumps and pens. Unfortunately, such technology has not been developed to a point to permit tightly controlled blood glucose levels. Inadequacy of the blood glucose sensors, as well as the dispensing mechanism, plague currently available automated insulin dispensers.

Others have attempted to control blood glucose levels in the diabetic patient by transplantation of pancreatic tissue from a donor to the diabetic patient. Major problems associated with such transplantations include: the shortage of donor tissue, the cost and expense involved in harvesting donor tissue, the need for immunosuppression to prevent tissue rejection in non-isograft transplantations, and the difficulty in maintaining viable tissue for prolonged periods of time after harvest. Even successful transplants suffer from the inherent autoimmune mechanism responsible for destruction of the patient's original islet beta-cells.

An alternate approach that has been suggested entails the use of a biohybrid perfused "artificial pancreas" comprised of islet tissue in a selectively permeable membrane. The selectively permeable membrane acts to protect the transplanted islets from being recognized and destroyed by the same autoimmune mechanism responsible for the destruction of the patient's original beta-cells. The in vivo treatment of diabetes with peritoneal implants of encapsulated islets has been reported by several research groups (See, e.g., U.S. Pat. No. 5,262,055 to Bae et al. (1993); U.S. Pat. No. 5,427,940 to Newgard (1992); Lum et al., Diabetes 40: 1511 (1991); Maki et al., Transplantation 51: 43 (1991); Robertson, Diabetes 40: 1085 (1991); Colton et al., J. Biomech. Eng. 113: 152 (1991); Scharp et al., Diabetes 39: 515 (1990); Reach, Intern. J. Art. Organs 13: 329 (1990)). Such artificial pancreases are expensive and time-consuming to fabricate, and have been found to exhibit limited usefulness in practice.

A considerable amount of research has also been undertaken with respect to the transplantation of beta-cell cell lines. Beta-cell cell lines typically have been generated from insulinomas and hyperplastic islets. Two main approaches have been used to isolate immortalized beta-cell lines: (1) isolating the cells from an X-ray induced rat insulinoma; (2) infection and transformation of a primary culture of islet cells by simian virus 40 (SV40). Several of these cell lines display insulin secretion characteristics similar to those observed in intact adult islets, in particular the response to glucose concentrations in the physiological range (5–15 mmol/L). A common problem associated with such cells lines is their phenotypic instability. That is, after propagation of the cells in culture, the cells frequently become responsive to subphysiological concentrations of glucose and/or manifest diminished insulin output.

As cells from immortalized cell lines are subject to the same autoimmunity that destroyed the host's beta-cells, such beta cell lines are commonly encapsulated for transplantation. While encapsulation reduces immunological response to the cells, because the cells themselves are undergoing rapid cell division, the increasing oxygen and nutrient demand within the encapsulation, as well as the increase in metabolic wastes, adversely impact the survivability of the cells.

Several researchers have proposed genetically altering immortalized beta cells to control proliferation. For example, U.S. Pat. No. 6,114,599 to Erfat discloses immortalized beta cells genetically engineered such that proliferation of the cells is regulated by the presence or absence of an antibiotic. Such cells are produced by introducing into the beta cell, a first gene comprising a DNA encoding a TetR-VP16 gene fusion protein, and an insulin promoter which controls expression of the fusion protein, and a second gene comprising a DNA encoding SV40 T antigen, and a tetracycline operator minimal promoter. Such stable integration of both genes is achieved and screening is performed for cells whose proliferation is controlled by tetracycline or a derivative thereof. Erfat and coworkers have suggested that controlled oncogenesis might be used to amplify human islet cells in vitro, with subsequent transplantation of the islet cells after oncogene inactivation.

U.S. Pat. No. 5,723,333 to Levine et al. (Issued: Mar. 3, 1998), teaches pancreatic cell lines established by transforming cells with vectors, preferably retroviral vectors, containing two or more oncogenes under the control of one or more inducible promoters and/or genetic elements. A subpopulation of such cells was found to express high levels of insulin. PCT Publication WO 01/11031 to Giannoukakis et al. (Published: Feb. 15, 2001) discloses genetically engineered beta-cells comprising nucleic acid molecules encoding inhibitors of interleukin-1β (IL-1β) signal transduction. IL-1β has been shown to be the initiating cytokine that is directly responsible for the impairment of glucose-stimulated insulin production in human islets in vitro (MacDaniel et al., Proc. Soc. Exp. Biol. Med. 211: 24 (1996)). By reducing IL-1β activity there is a corresponding reduction in beta-cell dysfunction and apoptosis in the diabetic animal. Nucleic acid molecules encoding biologically active proteins capable of inhibiting IL-1β are said to include IL-1Ra, NF-Kβ inhibitor, AP1 inhibitor, soluble forms of the IL-1R, mutant forms of the fas or FADD protein, IGF-1, the cowpox crmA protein, and members of the bcl-2 family such as Bcl-2 and Bcl-XL.

A number of researchers have attempted to reverse diabetes by inducing embryonic stem cells to develop into insulin-producing cells. Embryonic stem cells are primitive cells that under appropriate direction can develop into any cell type. While it has been demonstrated that fetal pig pancreatic tissue is able to normalize blood glucose levels in a rat, such occurs only several months after the transplantation and requires immunosuppression of the rat.

U.S. Pat. No. 5,837,236 to Dinsmore (Issued: Nov. 17, 1998), teaches that the life of fetal porcine pancreatic cells can be extended in xenogenic subjects when cell-surface antigens capable of eliciting an immune response in the xenogenic subject is altered to a non-immunogenic antigen. Studies are underway to determine artificial conditions under which such cells will develop into insulin-producing cells. Such approach suffers from the cost associated with isolating embryonic stem cells, the problem of introducing cross-species viruses along with a transplantation of tissue from one species to another, and with respect to human stem cells, the moral implications raised with respect to the use of such cells.

Short et al., Am. J. Physiology 275: E748 (1998) disclose an embryonic kidney cell line transformed by introduction of a replication-defective adenovirus comprising human proinsulin cDNA in which the dibasic prohormone convertase recognition sequence was altered to a tetrabasic furin cleavage site. Furin is an endogenous protease present in the constitutive secretory pathway of many cells. Such cells were found to synthesize both proinsulin and mature insulin. Injection of the viral construct into the external jugular vein of mice resulted in insulin gene expression in the liver, but improvement in the glycemic state was transient lasting about two to three weeks.

Stewart et al., J. Mol. Endocrin. 11, 335 (1993) disclose transfection of a murine pituitary cell line with a human preproinsulin DNA in a plasmid containing a metallothionein promoter and a gene conferring resistance to the antibiotic G418. Such cells when implanted into non-diabetic athymic nude mice were found to delay streptozotocin-induced hyperglycemia (streptozotocin destroying beta-cells) compared to control mice receiving an implant of the non-transfected cells. The implanted cells however were seen to form a tumor-like aggregation.

Valera et al., FASEB J. 8: 440 (1994) demonstrated that hepatocytes could be modified to harbor the human insulin gene under the control of the phosphoenolpyruvate decarboxylase gene. Transgenic animals harboring such hepatocytes were seen to fare significantly better than non-transgenic controls in maintaining euglycemia when challenged with streptozotocin. Ectopic expression of insulin in hepatocytes of diabetic rats has also been reported by Kolodka et al. (Proc. Natl. Acad. Sci. 92: 3293 (1995) using in vivo retroviral gene transfer.

PCT Publication WO 97/14441 to Pollock et al. (Published: Apr. 24, 1997) teaches engineered cells expressing an exogenous or endogenous insulin gene in addition to an exogenous calbindin gene. Pollock et al. indicate that such cells exhibit the ability to secrete insulin in a glucose-sensitive fashion. They disclose that the cells may be enclosed in a semipermeable porous matrix which may be implanted into a diabetic animal to ameliorate insulin supplementation needs.

Sugiyama et al., Horm. Metab. Res. 29: 599 (1997), report transfection of hepatocytes with the rat insulin gene and lacZ using a defective adenoassociated viral (AAV) vehicle. Such cells are said to cause a reduction in glucose concentrations in surrounding medium and when transfected in vivo, a decrease in blood glucose levels Bartlett et al. (Transplantation Proceedings: 29, 2199 (1997)) disclose an expression vector which when injected directly into the hamstring muscle of normal or diabetic rats release proinsulin for up to 12 weeks. The vector comprises proinsulin genomic DNA inserted into the pAAV-CKM vector immediately after the CKM promoter.

U.S. Pat. No. 5,811,266 to Newgard (Issued: Sep. 22, 1998) discloses artificial beta-cells achieved through the introduction of one or more genes selected from the insulin gene, glucokinase gene, and glucose transporter gene, to provide an engineered cell having all three of the genes in a biologically functional and responsive configuration. Glucokinase, and the facilitated-diffusion type glucose transporter known as GLUT-2, are believed to be involved in the control of glucose metabolism in beta-cells.

PCT Publication WO 99/54451 to Powers et al. (Published: Oct. 28, 1999) teaches neuroendocrine cells secreting insulin. The engineered neuroendocrine cells which secrete insulin in response to glucose comprise a gene encoding a non-glucose insulin secretagogue receptor and an exogenous insulin gene. At least one of the genes is a recombinant gene introduced into the cell by means of a recombinant vector. It is hypothesized by the inventors that the ability of neuroendocrine cells to correctly process insulin reflects expression of similar hormone processing enzymes in a variety of neuroendocrine cells. The non-glucose insulin secretagogue receptors are said to include receptors for glucagon-like peptide 1, glucose-dependent insulin releasing polypeptide, cholecystokinin, gastrin, secretin, and gastric inhibitory peptide. Preferred cells for transformation are said to have an inherent capability of forming secretory granules, such as those from the pituitary and thyroid glands.

PCT Publication WO 00/31267 to Bosch et al. (Published: Jun. 2, 2000) teaches transfecting a precursor muscle cell or myoblast cell line with an exogenous gene encoding insulin. Preferred cell lines are myoblast cell lines like C2C12 which rapidly divide in the myoblast state and have the potential for differentiating into non-dividing myotubes. Such cells are said to be amenable to production in large quantities in the myoblast state, and after differentiation, capable of producing recombinant proteins with the use of a suitable promoter while not dividing. The promoter sequence is selected such that the promoter is activated or induced during diabetic conditions in the patient, and includes myosin light chain promoters, creatine kinase and myoD.

Lee et al., Nature 408: 483 (2000), report a recombinant adeno-associated virus (rAAV) capable of transforming a cell to express a single-chain insulin analogue ("SIA"), formed by replacing thirty-five residues of the C-peptide with a short turn-forming heptapeptide, which possess biologically-active insulin activity without enzymatic conversion, under the control of hepatocyte-specific L-type pyruvate kinase (LPK) promoter which regulates SIA expression in response to blood glucose levels. An albumin leader sequence was added to the SIA gene construct to facilitate the secretion of SIA from the cells, while the simian virus 40 enhancer (SV40) was added downstream of the SIA gene in order to elevate the basal level of SIA expression. The recombinant adeno-associated virus was found to cause the remission of diabetes in streptozotocin-induced diabetic rats and autoimmune diabetic mice for a prolonged time.

Barry et al., Human Gene Therapy 12: 131 (Jan. 20, 2001), have shown that retroviral vectors encoding glucose-responsive promoters driving furin expression may provide an amplified, glucose-regulated secretion of insulin. The group discloses a LhI*TFSN virus construct encoding a glucose-regulatable rat transforming growth factor α (TGFα) promoter controlling murine furin expression with a viral long terminal repeat promoter (LTR) driving constitutive expression of furin-cleavable human proinsulin. When such construct was transduced into vascular smooth muscles cells, the cells were seen to respond to physiological glucose concentrations. The furin-cleavable human proinsulin was obtained by altering human proinsulin cDNA to encode furin-cleavable sites (Hosaka et al., J. Biol. Chem. 255: 12127 (1991); Groskruetz et al., J. Biol. Chem. 269: 6241 (1994); Gros et al., Gene Ther. 8: 2249 (1997)). A selectable neo gene (bacterial neomycin phosphotransferase) was incorporated into the construct with the neo gene being expressed from and driven by the simian virus 40 promoter (SV40). Insulin release from the cells was adjudged against cells transduced with retroviral vectors comprising the LTR promoter driving either human adenosine deaminase cDNA or rat erythropoietin cDNA, and a SV40 promoter driving the selectable neo gene. Genetically altered cells were placed in a collagen matrix and implanted into a small pocket made in the stomach capsule of congenic DR lyp/lyp BB rats that had become diabetic (blood glucose exceeding 180 mg/dl). In eight treated rats, the researchers found a major reduction in insulin requirement to as low as 25% of pretreatment level for up to three months, with one rat becoming insulin free without hypoglycemia. Intraperitoneal glucose tolerance tests in diabetic rats receiving controlled cell implants did not show the characteristic decline in blood glucose of normal rats after glucose administration.

Numerous problems plague prior art "artificial beta-cells." Such cells are typically very difficult to culture and are seen in practice to frequently loose their functional capabilities very quickly in culture. The majority of such cell lines either do not secrete sufficient insulin to be therapeutic or the insulin production is unregulated. In those cell lines that have shown some degree of glucose-regulated insulin production, most often a glucose responsive promoter transcriptionally regulates the insulin gene directly, failing to produce the C-peptide that has been reported to possess vasculature and neurologic functions. Transplantation of genetically-altered cells of the prior art typically also require the use of immune suppressing drugs for life, or incorporation into an immunoisolation device wherein prior art cells have frequently been found to be less than effective due to overgrowth or rapid senescence in the device.

There is a great need, therefore, for improved cell lines that are programmed to produce insulin in a glucose-responsive manner, that can produce mature insulin as well as the C-peptide that is reported to possess vasculature and neurologic functions, and that are adapted for growth to function over a significant period of time in an immunoisolation device so that no immunosuppression is required with respect to the transplant recipient.

SUMMARY OF THE INVENTION

In order to overcome many of the disadvantages associated with the prior art, there is disclosed herein a recombinant nucleic acid construct having multifunctional sequences (herein referred to as a "cassette") useful for engineering cells that secrete insulin in response to glucose. Such nucleic acid construct is particularly useful for introducing insulin secretory capacity into non-beta cells. Also disclosed are recombinant, glucose-regulated, insulin-producing cells wherein insulin secretion is significantly regulated at the level of pro-insulin processing. Further disclosed are recombinant, glucose-regulated, insulin-producing cells capable of secreting mature insulin as well as the C-peptide from proinsulin. And yet in another embodiment of the present invention there is disclosed cell lines adapted for growth in an immunoisolation device.

The nucleic acid constructs of the present invention use systems in unique combinations and orientations to cause glucose-regulated production of human insulin. Various types of expression control sequences and genes are harnessed in the constructs of the present invention to effect expression of human proinsulin and to regulate its cleavage at the C-peptide, and to produce insulin by way of a glucose-activated promoter of a proinsulin protease.

In preferred embodiments of the present invention, the nucleic acid construct comprises a human proinsulin nucleotide sequence that is altered to encode a human proinsulin having altered protease cleavage sites from wild-type. It is further preferred that the genetic constructs of the present invention further comprise a nucleotide sequence encoding a human protease having affinity for the altered protease cleavage sites. Advantageously, the human proinsulin nucleotide sequence that is altered at its protease cleavage sites further comprises a variant, such as an H10D variant (i.e., histidine to aspartic acid at position 10 in the B chain) (described in U.S. patent Ser. No. 4,992,418), that increases the affinity of the mature insulin for insulin-receptor binding sites.

In one embodiment of the present invention, there is provided a nucleic acid construct comprising a human proinsulin nucleotide sequence that is altered to encode a human proinsulin having altered protease cleavage sites from wild-type, a nucleotide sequence encoding a human protease having affinity for the altered protease cleavage sites, the nucleotide protease sequence preferably being preceded by a translation initiation sequence to allow proper translation initiation, a constitutive promoter positioned with respect to the altered human proinsulin sequence so as to be capable of promoting its transcription upon activation of the promoter, and a glucose-responsive promoter positioned with respect to the nucleotide protease sequence so as to promote its transcription upon activation by the insulin secretagogue, glucose.

A particularly advantageous construct of the present invention employs a nucleotide sequence, which may be cDNA, encoding for the expression of human proinsulin that is altered to incorporate altered subtilisin-like serine protease-cleavable cleavage sites, a promoter of the transcription of the altered human proinsulin nucleotide sequence, a nucleotide sequence encoding a human subtilisin-like serine protease capable of cleavage at the altered cleavage sites, a glucose-regulated promoter of the transcription of the human furin nucleotide sequence, and a translation initiation nucleotide sequence, such as a consensus Kozak sequence, operatively positioned with respect to the human furin nucleotide sequence to allow proper translation upon transcription of the same. The nucleotide sequence encoding the subtilisin-like serine protease may advantageously encode furin.

In one embodiment of the present invention, there is provided a nucleic acid construct comprising one or more viral long terminal repeat (LTR) promoter-enhancers, a nucleotide sequence encoding human proinsulin that is artificially altered at its protease cleavage sites to accommodate the specificity of a subtilisin-like serine protease, such altered proinsulin nucleotide sequence being under the control of a LTR promoter-enhancer; a nucleotide sequence encoding a human subtilisin-like serine protease, such as furin; a translation initiation nucleotide sequence, such as a consensus Kozak sequence, operatively positioned with respect to the human furin nucleotide sequence to allow proper translation upon transcription of the same; and a glucose-regulatable promoter, such as transforming growth factor α (TGF-α) promoter, positioned with respect to the nucleotide sequence encoding human furin so as to promote its transcription. The LTR promoter-enhancers may optionally be deleted if a non-viral construct is desired.

In another embodiment of the present invention there is provided a nucleic acid construct for transforming cells comprising a viral LTR promoter-enhancer, a nucleotide sequence encoding human proinsulin that is artificially altered at its protease cleavage sites to accommodate the specificity of furin, the proinsulin encoding nucleotide sequence being under control of the viral LTR promoter-enhancer, a transforming growth factor α (TGF-α) promoter, a nucleotide sequence encoding human furin flanked 5' by a translation initiation nucleotide sequence, such as a consensus Kozak sequence, the furin-encoding, flanked nucleotide sequence being under the control of the (TGF-α) promoter, a simian virus 40 (SV40) promoter, a nucleotide sequence encoding neomycin phosphotransferase (Neo), the neomycin phosphotransferase nucleotide sequence being under the control of the SV40 promoter, and a viral LTR promoter-enhancer 3' of the Neo nucleotide sequence.

And yet in another embodiment of the present invention, there is provided nucleic acid constructs as described above, further comprising a cytomegalovirus (CMV) promoter operably linked to the nucleotide sequence encoding human proinsulin that is artificially altered at its protease cleavage sites to accommodate the specificity of furin so as to drive constitutive expression of the altered human proinsulin. The CMV promoter is optionally operably-linked to a LTR promoter-enhancer such that the LTR cis-regulatory sequence can elevate transcription due to the CMV promoter. In such construct, the CMV promoter is used to drive constitutive expression of the altered human proinsulin while the LTR promoter-enhancer is used to enhance transcription from the CMV promoter. The LTR promoter-enhancer may be modified as known in the art to improve the level of expression of the altered human proinsulin (See, e.g., Hillberg, et al., PNAS USA 84: 5232 (1987); Holland, et al., PNAS USA 84: 8662 (1987); Valerio, et al., Gene 84: 419 (1989)).

And yet in another preferred embodiment of the present invention, there is provided a nucleic acid construct comprising a nucleotide sequence encoding human proinsulin that is artificially altered at its protease cleavage sites to accommodate the specificity of furin; a CMV promoter operatively-linked to promote the transcription of the altered human proinsulin nucleotide sequence; a polyadenylation site located 3' to the human proinsulin nucleotide sequence, a nucleotide sequence encoding human furin; a glucose-regulatable promoter, such as a TGF-α promoter, operatively-linked to the nucleotide sequence encoding human furin so as to promote its transcription with increasing glucose concentrations; a polyadenylation sequence located 3' to the nucleotide sequence encoding human furin; a nucleotide sequence encoding for a selectable marker, such as neomycin phosphotransferase; a constitutive promoter, such as SV40, operatively linked to the nucleotide sequence encoding the selectable marker so as to promote its transcription; and a polyadenylation sequence located 3' to the nucleotide sequence encoding the selectable marker.

As would be appreciated by one of ordinary skill in the art, the present invention may be extended to transgenic animals and microorganisms incorporating the described nucleic acid constructs, and such extension is contemplated herein. As would be also appreciated by one of ordinary skill in the art, transformation of target cells by the nucleic acid constructs described herein may be accomplished using one or more vectors. For example, instead of incorporation of the nucleic acid construct into one vector and transforming the cell therewith, one could transform the cells with one vector comprising a nucleotide sequence encoding human proinsulin that is artificially altered at its protease cleavage sites to accommodate the specificity of furin and a promoter-enhancer operably linked to the proinsulin-encoding nucleotide sequence so as to be able to promote/enhance transcription of such sequence, and yet another vector comprising a nucleotide sequence encoding human furin flanked 5' by a consensus Kozak sequence, and a glucose-sensitive promoter-enhancer operably-linked to the furin-encoding, flanked nucleotide sequence so as to be able to promote/enhance transcription of the such sequence. In such dual vector transformation, it would be preferred that each vector contain a different dominant selectable marker, allowing selection of a target cell that has been transfected by both vectors.

DETAILED DESCRIPTION OF THE INVENTION

Figure 1:
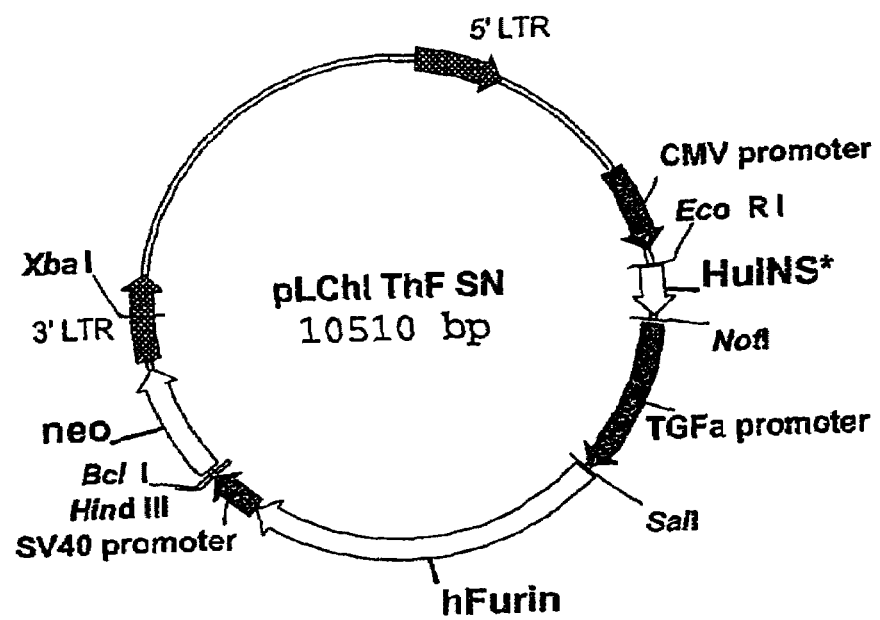
FIG. 1 illustrates an expression plasmid comprising a CMV promoter in conjunction with an LTR promoter-enhancer driving constitutive expression of a altered human proinsulin, a TGF-α promoter promoting transcription of a nucleotide sequence encoding human furin, and a selectable marker unit comprising a nucleotide sequence encoding neomycin phosphotransferase (Neo), the transcription of which is promoted by a SV40 promoter and enhanced by an LTR.

1. Definitions:

The following definitions are provided to facilitate understanding of certain terms used herein:

By "cells" it is meant to include cells in any form, including, but not limited to, cells retained in tissue, cell clusters and individually isolated cells.

By "cell line" it is meant cells capable of stable growth in vitro for many generations.

By "clone" it is meant a population of cells derived from a single cell or common ancestor by mitosis.

By "CMV promoter" it is meant a promoter isolated from cytomegalovirus ("CMV"), an enveloped icosahedral virus that contains double stranded DNA, and variants thereof. Cytomegalovirus is of the herpesviridae group.

By "consensus sequence" it is meant the sequence of a series of related, DNA, RNA or protein sequences, that reflects the most common choice of base or amino acid at each position.

By "constitutive promoter" it is meant a promoter the action of which is not regulated by a substrate.

By "expression control sequence" it is meant a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

By "exogenous" material it is meant material that has been introduced into a cell, organism etc. that originated outside of the same.

By "expression cassette" it is meant a nucleic acid construct, generated recombinantly or synthetically, with a series of specified nucleic acid elements which permit transcription of a particular nucleic acid in a target cell. Typically, an expression cassette in an expression vector comprises a polynucleotide operably linked to transcriptional initiation regulatory sequences that direct the transcription of the polynucleotide in the intended host cell.

By "expression vector" it is meant a vector that has been designed to express cloned genes in a particular cell.

By "furin" it is meant the subtilisin-like eukaryotic endopeptidase with substrate specificity for consensus sequence Arg-X-Lys/Arg-Arg, and variants thereof.

By "gene" it is meant the set of DNA sequences that are required to produce the single polypeptide referenced. For example, by "abscisic acid responsive element-binding factor 4" gene it is meant the DNA sequence that comprises the exons required to produced abscisic acid responsive element-binding factor 4. By "gene" it is meant to include DNA sequences encoding variants of the polypeptide.

By "glucose-regulatable promoter" it is meant a promoter the action of which is regulatable by glucose.

By "insulin" it is meant insulin and variants thereof. Likewise by the terms "proinsulin" and "preproinsulin" it is meant to include variants thereof.

By "isolate" a material it is meant changing the environment of the material or removing a material from its original environment, or both. For example, when a polynucleotide or polypeptide is separated from the coexisting materials of its natural state, it is "isolated."

By "Kozak consensus nucleotide sequence" it is meant a nucleotide sequence encoding the consensus for the translational start site of mRNA in eukaryotes for efficient translation (Kozak, Nuc. Acid Res. 12, 3873–3893, 1984).

By "long-terminal repeat" is meant identical DNA sequences, several hundred nucleotides long, found at either end of transposons and the proviral DNA formed by reverse transcription of retroviral RNA. Long terminal repeats have inverted repeats, that is, sequences close to either end that are identical when read in opposite directions. In proviruses, the upstream long-terminal repeat acts as a promoter and enhancer and the downstream long-terminal repeat as a polyadenylation site.

By "operably-linked" or "operatively linked" nucleotide sequences it is meant a juxtaposition such that the functionality of the sequences is preserved. Thus, for example, a coding sequence "operably linked" to a promoter is positioned so that the promoter is capable of effecting the expression of the coding sequence.

By "polynucleotide" it is meant any polyribonucleotide or polydeoxyribonucleotide, which may be unmodified RNA or DNA, or modified DNA or DNA. As used herein, "polynucleotide" include, without limitation, single- and double-stranded DNA and RNA, hybrid molecules comprising DNA and RNA that may be single-stranded, or more typically double-stranded, or a mixture of single- and double-stranded regions. The term "polynucleotide" further may refer to triple-stranded regions comprising RNA or DNA or both DNA and RNA. "Polynucleotide" embraces chemically, enzymatically or metabolically modified forms of polynucleotides typically found in nature, as sell as chemical forms of DNA and RNA characteristic of viruses and cells. The term is meant to encompass both long nucleotide as well as short nucleotide sequences, often referred to as oligonucleotides, and oligomers.

By "promoter sequence" it is meant a DNA regulatory region capable of binding RNA polymerase in a cell and initiating transcription of a downstream (3' direction) coding sequence. Within the promoter sequence will be found a transcription initiation site, as well as protein binding domains responsible for the binding of RNA polymerase. The nucleotide region at which transcription starts is designated +1, and nucleotides are numbered from this position with negative numbers indicating upstream nucleotides and positive downstream nucleotides.

By "recombinant" or "engineered" cell it is meant a cell into which a recombinant gene has been introduced through the hand of man. Recombinantly introduced genes may be in the form of a cDNA gene (i.e., lacking introns), a copy of a genomic gene (i.e., including introns with the exons), genes produced by synthetic means, and/or may include genes positioned adjacent to a promoter, or operably linked thereto, not naturally associated with the particular introduced gene.

By "replicon" it is meant any genetic element (e.g., plasmid, chromosome, virus) that functions as an autonomous unit of DNA replication in vivo, i.e. capable of replication under its own control.

By "secretagogue" it is meant a substance that induces secretion from cells.

By "structural gene" it is meant a gene that codes for a product (e.g., an enzyme, structural protein, tRNA) as opposed to a gene that serves a regulatory role.

By "SV40" promoter it is meant the Simian Virus 40 promoter, a small DNA-containing tumor virus of the group papovavirus, and variants thereof.

By "therapeutically effective amount" it is meant an amount sufficient to ameliorate a condition in a clinically-useful positive manner.

By "transformed cell" it is meant a cell into which exogenous or heterologous DNA has been introduced. The transforming DNA may or may not be integrated (covalently linked) into chromosomal DNA making up the genome of the cell. The transforming DNA may be maintained on an episomal element such as a plasmid.

By "TGF-α" it is meant the 50 amino acid polypeptide transforming growth factor originally isolated from viral-transformed rodent cells that contains an EGF-like domain and binds to EGF receptor, and variants thereof, such polypeptide stimulating the growth of microvascular endothelial cells, and variants thereof.

By "transfection" it is meant the introduction of a nucleic acid sequence into a target cell.

By "transforming growth factor" it is meant a protein secreted by transformed cells that can stimulate growth of normal cells.

By "translation initiation nucleotide sequence" it is meant a nucleotide sequence encoding the initiation site for mRNA translation.

By "variant" it is meant a sequence, such as a polynucleotide or polypeptide, that differs from another sequence, but retains essential properties thereof, that is, properties for which the sequence is utilized in its application (e.g., promoting expression, cleaving a bond, etc.). For example, a variant of a polynucleotide may differ in nucleotide sequence by one or more substitutions, additions, and deletions, from the reference polynucleotide. By "variant" it is also meant to include a fragment of a full length sequence that retains essential properties thereof.

By "vector" it is meant a replicon, such as a plasmid, phage, phagemid or cosmid, used for the transformation of cells in gene manupulation. Vectors may include nucleotide molecules from different sources which have been artificially cut and joined.

2. The Construct

The present invention overcomes many of the problems associated with prior art methods for ameliorating the diabetic state. By using unique combinations of different DNA sequences, the present invention permits a nucleic acid construct that can be used to transform cells, in particular somatic cells, to secrete insulin in a glucose-regulated fashion.

The present invention describes a nucleic acid construct that comprises a nucleotide sequence that is altered to provide for the expression of a human proinsulin that has protease cleavage sites altered from wild-type to have increased affinity for a human protease having activity at the altered protease cleavage site, a nucleotide sequence encoding the human protease, the nucleotide sequence encoding the human protease being preceded by a translation initiation nucleotide sequence to proper translation initiation, a constitutive promoter positioned with respect to the altered human proinsulin sequence so as to be capable of promoting its transcription upon activation of the promoter, and a glucose-responsive promoter positioned with respect to the nucleotide sequence encoding the human protease so as to promote its transcription upon activation by glucose.

In an embodiment, the present invention comprises a promoter to drive constitutive expression of the altered cleavage site human proinsulin nucleotide sequence. The constitutive promoter can be any promoter useful in the constructs of the present invention for driving expression of a furin-cleavable insulin including but not limited to: cytomegalovirus (CMV), phosphoglycerate kinase (PGK), and elongation factor 1 (EF1). Other promoters useful in the constructs of the invention can be determined by methods known in the art, such as insulin radioimmunoassay. The constitutive promoter is advantageously operably linked to an enhancer, such as the Long Terminal Repeat ("LTR") promoter-enhancer ("LTR"), which elevates levels of its transcription. Such promoter-enhancer, however, may be avoided when a non-viral construct is desired. Expression of the altered human proinsulin may further be improved by polyadenylation of the 3' end of the nucleotide sequence encoding the altered human proinsulin.

The human protease comprising the altered human proinsulin protease cleavage sites is preferably a subtilisin-like serine protease, advantageously furin. The expression of the human protease can be significantly improved by incorporation of translation initiation nucleotide sequence positioned 5' to the nucleotide sequence encoding the subtilisin-like serine protease in such a manner as to proper translation. A preferred translation initiation nucleotide sequence is a nucleotide encoding the Kozak consensus sequence or variant thereof. The addition of poly-A to the 3' end of the nucleotide sequence encoding the human subtilisin-like serine has also been seen to improve expression.

A preferred glucose-regulatable promoter is a transforming growth factor promoter. The TGF-α promoter has been found to be particularly useful in the glucose regulated expression of human subtilisin-like serine proteases, in particular furin.

The construct preferably also comprises a nucleotide sequence encoding a product that allows for easy selection of transformed cells. For example, a nucleotide sequence encoding neomycin phosphotransferase ("Neo") may be incorporated into the construct permitting selection of transformed cells by growth in neomycin containing medium. Neo transcription can be promoted by a promoter, such as the simian virus 40 (SV40) promoter. Activity of the promoter may be advantageously enhanced by operable-linkage of the promoter to a promoter/enhancer such as LTR (LTR sequences may be avoided when a non-viral construct is desired). Polyadenylation at the 3' end of the nucleotide sequence encoding Neo can be employed to increase expression of Neo.

As would be understood by the skilled artisan, the order of the nucleotide sequences and promoter in the constructs of the present invention can be altered, for example, expression of the maker can be driven by the 5'LTR or SV40, i.e., pLChI*ThFSN or pLNChI*ThF.

3. Insulin Expression in Transformed Cell Lines

The above described nucleic acid constructs may be used to transform cells so as to produce insulin expressing cell lines. Generally, any system or vector suitable to express the polypeptides of the nucleic acid construct may be employed. Introduction of the construct may be effectuated by any of the methods well known to those of ordinary skill in the art, as described, for example, in Sambrook et al., Molecular Cloning: A Laboratory Manual, 2d Ec., Cold Spring Harbor Press, Cold Spring Harbor, N.Y. (1989). As would be understood by the skilled artisan, such methods include, without limitation, calcium phosphate transfection, DEAE-dextran mediated transfection, microinjection, cationic lipid-mediated transfection, electroporation, transduction, scrape loading, ballistic introduction or infection.

Human proinsulin may be altered at its protease cleavage sites using techniques known to those of ordinary skill in the art, such a site-directed mutagenesis (using, for example, Unique Site Elimination Mutagenesis Kit, Pharmacia). A human cDNA sequence encoding proinsulin may be obtained, for example, from plasmid pCHI-I (Bell et al., Nature 282: 525 (1979)) by polymerase chain reaction ("PCR"). Furin cleavage sites (Arg-X-(Lys/Arg)-Arg) may be introduced at both the B-C junction and the C-A junction such as described in Gros et al., Human Gene Therapy 8: 2249 (1997). A change of His-10 to Asp in the B peptide is also preferably made so as to enhance stability of the mature insulin product (See, Groskreutz et al., J. Biol. Chem. 269: 6241 (1994)).

In a preferred embodiment, the construct is cloned into a plasmid. Viral expression vectors may also be used.

Groskreutz et al., J. Biol. Chem. 269:6241 (1994) have previously reported that when an adenovirus transformed human kidney cell line 293 ("HEK-293") is transformed with a plasmid encoding altered human proinsulin having furin cleavable sites, mature insulin could be obtained, presumably due to furin present in the constitutive secretory pathway. However, the authors could not be certain whether cleavage was due to the furin or other protease produced by the HEK-293, for example, PACE4 (PACE4 is Furin).

Vollenweider et al., Diabetes 44: 1075 (1995), have described co-transfecting, using the calcium phosphate precipitation method. (Graham et al., Virology 52: 456 (1973)), Monkey Kidney (COS-7) cells with a first plasmid encoding for human proinsulin altered to incorporate furin cleavage sites, and a second plasmid encoding mouse furin. When the first plasmid alone was used to transform the COS-7 cells, proinsulin was the major immunoreactive form detected. However, when both plasmids were co-transfected, mature insulin was the major immunoreactive form detected. When co-transfection lead to co-transformed cells expressing the exogenous protease furin, the majority (>60%) of immunoreactive form seen was fully-processed ("mature") insulin.

Recently, Barry et al., Human Gene Therapy 12: 131 (Jan. 20, 2001) have reported the construction of a vector comprising a nucleotide sequence encoding human proinsulin altered at its protease cleavage sites to allow for expression of a furin-cleavable human proinsulin, a viral LTR promoter driving constitutive expression of the furin-cleavable human proinsulin, a nucleotide sequence encoding mouse furin cDNA, a human transforming growth factor a promoter of transcription of the mouse furin cDNA, and a selectable nucleotide sequence encoding bacterial neomycin phosphate, transcription of such nucleotide sequence being constitutively promoted by a SV40 promoter and enhanced by a LTR promoter-enhancer. When such construct was used to transform vascular smooth muscle, transformed cells were seen to secrete both proinsulin as well as mature insulin. Diabetic rats receiving insulin-secreting cells transformed with such construct require significantly less insulin to obtain normal insulin levels. A nearly 3-fold increase in mature insulin secretion in low-glucose conditioned media was seen as compared to cells grown on high glucose media.

The present invention greatly improves the mature insulin expression levels, and degree of glucose sensitivity, of transformed cells over the constructs and systems of Groskreutz et al., J. Biol. Chem. 269:6241 (1994), Vollenweider et al., Diabetes 44: 1075 (1995), and Barry et al., Human Gene Therapy 12: 131 (Jan. 20, 2001).

In one aspect of the present invention, the inventors have unexpectedly discovered significantly enhanced insulin:proinsulin levels produced by cells transformed with proinsulin: furin constructs comprising a nucleotide sequence encoding proinsulin under the control of a constitutive promoter, and a nucleotide sequence encoding human furin under the control of a glucose-regulatable promoter.

With respect to the murine furin nucleotide sequence of pLhI*TFSN (Barry et al., Human Gene Therapy 12: 131 (2001)) derived from pSVLFur (American Type Culture Collection ("ATCC")), the present inventors have unexpectedly discovered an approximately 300 bp sequence at the 3' end of the reputed gene sequence which does not encode for murine furin. Such base pair sequence on analysis was discerned to include portions of the luciferase gene coding region comprising an additional ATG start site. Incorporation of the extra ATG site is believed to have decreased efficiency in transcription. Removal of the approximately 300 bp sequence substantially improved the conversion of proinsulin into mature insulin. After removal of the sequence the vector comprising the nucleotide sequence encoding mouse furin was seen to produce mature insulin in HEK-293T cells at approximately the same level as the same construct comprising instead a nucleotide sequence encoding human furin.

Further improvement in mature insulin production was found by operably linking a strong promoter to the nucleotide sequence encoding the altered proinsulin, in particular the CMV promoter. Operable linkage of the CMV promoter to the LTR promoter-enhancer was seen to result in very large increases in mature insulin production with respect to the transformed cells. The degree of this change (over 100 fold) was entirely unexpected.

Turning to FIG. 1 there is shown an expression vector of the present invention (designated pLChI*ThFSN) useful for transforming cells where:

L is a 5' LTR promoter-enhancer;
C is a CMV promoter.
hI* is cDNA encoding for human proinsulin altered so as to have furin cleavable sites at its B-C and C-A junctions and carrying a H10D variant;
T is a human or murine TGF-α promoter;
hF is a nucleotide sequence encoding for human furin;
S is a SV40 promoter; and
N is a nucleotide sequence encoding for neomycin phosphotransferase, a selectable marker gene.

Figure 3:
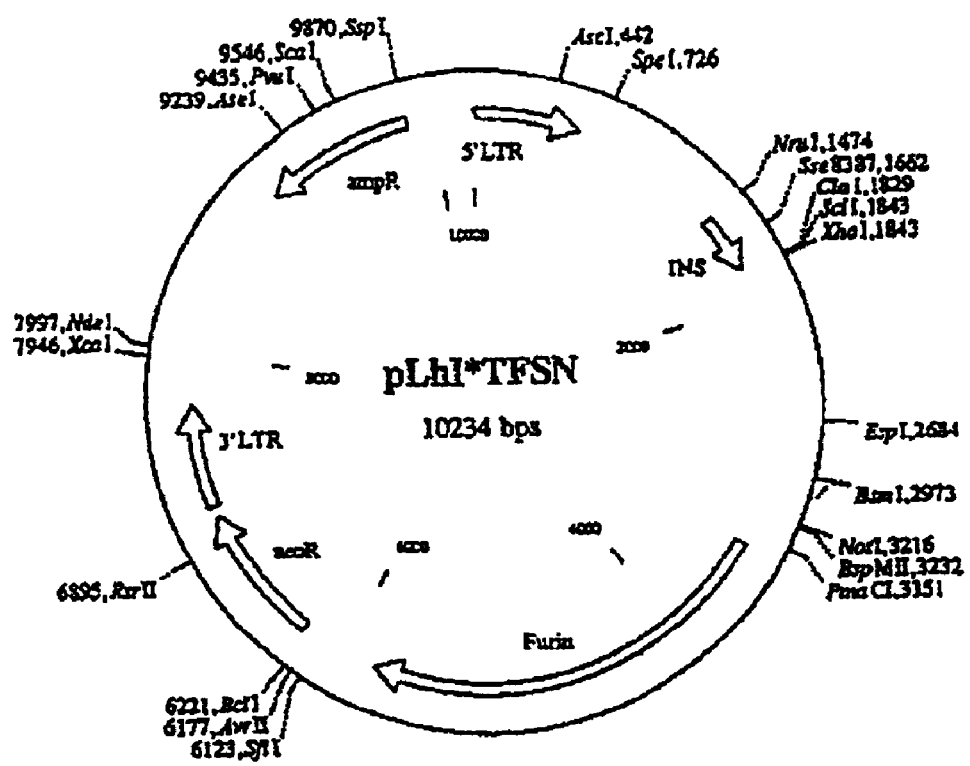
FIG. 3 diagrammatically describes the construct of the expression plasmid pLhI*TFSN.

As seen in Table I, the expression vector of FIG. 1 when transfected into HEK-293T cells grown in DMEM supplemented with 10% FBS medium resulted in a concentration of mature insulin in the medium that was augmented by two orders of magnitude when compared to the vector of Barry et al. (Human Gene Therapy 12: 131 (2001)) whether such construct was designed to express human or murine furin. A diagrammatic representation of pLhI*TFSN is set forth at FIG. 3, wherein INS is the nucleotide sequence encoding for human proinsulin altered to have furin cleavable-sites at its B-C and C-A junctions and having an H10D variant, Furin is the nucleotide sequence for human furin, and NeoR is the nucleotide sequence encoding for neomycin phosphotransferase.

TABLE I

| VECTOR | CONCENTRATION OF INSULIN IN MEDIUM |
| --- | --- |
| pLhI*TmFSN | 17 μIU/ml |
| pLhI*ThFSN | 12 μIU/ml |
| pLChI*ThFSN | 1360 μIU/ml |
| pLChI*ThFSN | 1653 μIU/ml |
| pLNChI* 6 (parent, no furin) | 14 |
| pLNChI* 6.1 | 299 |
| pLNChI* 6.2 | 316 |
| pLNChI* 6.4 | 305 |
| pLNChI* 6.6 | 589 |

Figure 2:
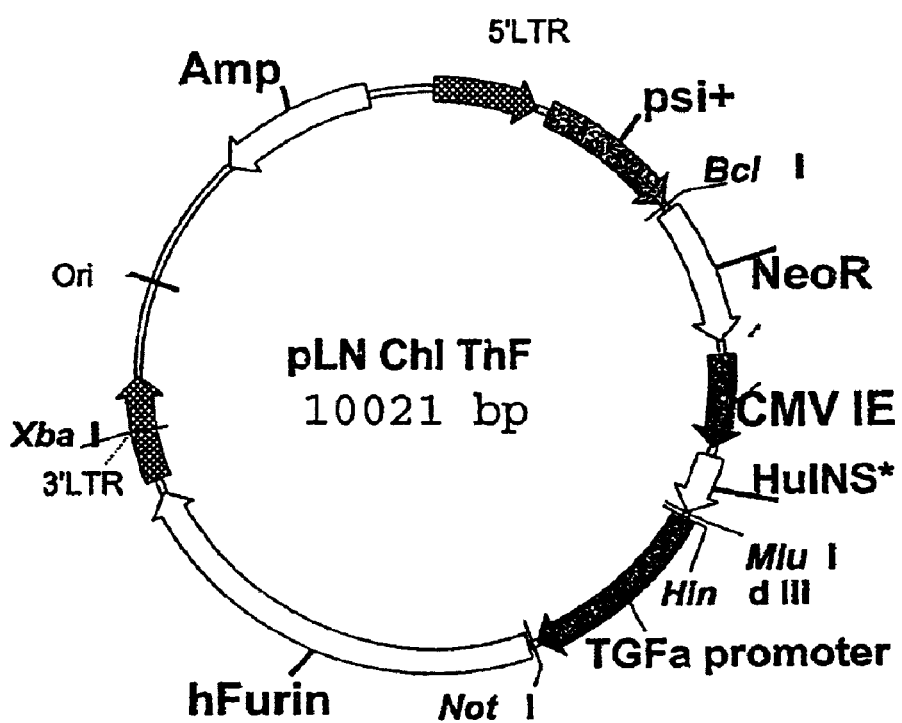
FIG. 2 illustrates an expression plasmid of the present invention similar to the construct of FIG. 1 but where the order of the three genes is altered such that Neo expression is driven by the 5'LTR and expression of human insulin is driven by the CMV promoter.

FIG. 2 illustrates an expression plasmid of the present invention (designated pLNChI*ThF) similar to the construct of FIG. 1 but where the order of the three genes is altered such that Neo expression is driven by the 5'LTR and expression of human insulin is driven by the CMV promoter. As seen in Table I, the expression vectors of FIG. 2 when transfected into HEK-293T cells grown in DMEM supplemented with 10% FBS medium resulted in a concentration of mature insulin in the medium that was augmented by 21 to 42 fold when compared to the pLNChI* 6 (parent, no furin) and at least 17 fold when compared to the vector of Barry et al.

The present inventors have further designed a non-viral construct lacking LTR sequences which produces significantly higher amounts of mature insulin than the retroviral vectors of Barry et al., Human Gene Therapy 12:131 (2001). In such construct there is provided: (a) a proinsulin expression cassette comprising a nucleotide sequence encoding human proinsulin altered to incorporate furin-cleavable sites at its B-C and C-A junctions, a polyadenylation site 3' to the altered human proinsulin nucleotide sequence and a promoter operably linked to the altered human proinsulin nucleotide sequence; (b) a human furin expression cassette comprising a nucleotide sequence encoding human furin capable of cleaving the altered sites of the proinsulin encoded by the proinsulin expression cassette, a polyadenylation site 3' to nucleotide sequence encoding the human furin, and a promoter; and (c) a selectable marker expression cassette comprising a nucleotide sequence comprising a selectable marker, and promoter of such selectable marker. In an embodiment the promoter which drives expression of the altered human proinsulin is CMV. In another embodiment the promoter which drives expression of human furin is TGF-α. In a preferred embodiment the selectable marker is neomycin phosphotransferase, which will permit cells to grown in culture medium comprising G418. In another preferred embodiment the promoter of the selectable marker is SV40. It is further preferred the selectable marker sequence be followed 3' by a polyadenylation site.

Figure 4:
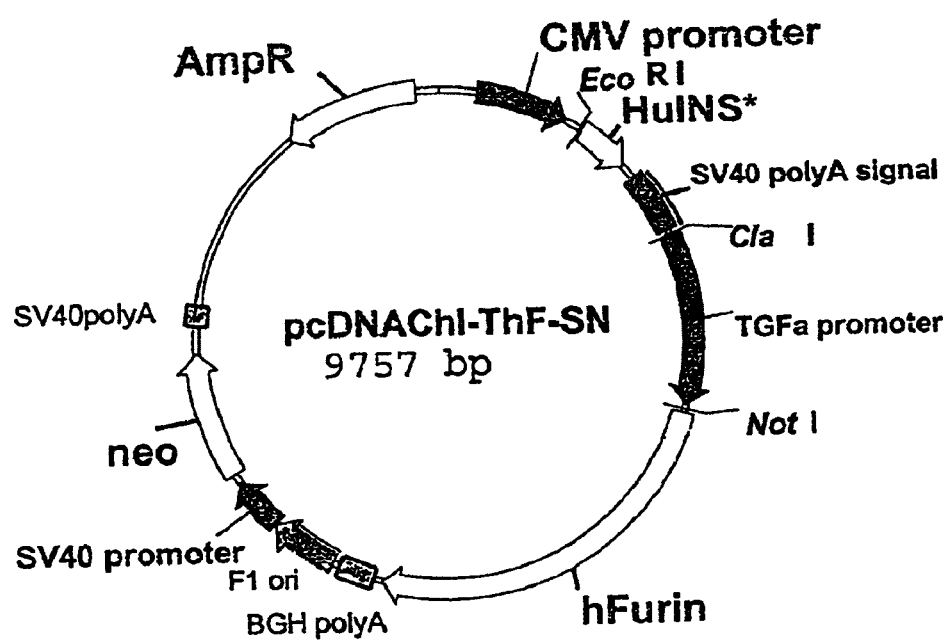
FIG. 4 illustrates an expression plasmid of the present invention similar to the construct of FIG. 1 but including polyadenylation sequences 3' to each of the structural genes, and lacking LTR repeats.

Turning to FIG. 4 there is shown an expression vector of the present invention (designated pcDNAChI*ThFSN) useful for transforming cells where:

C is a CMV promoter.

hI* is cDNA encoding for human proinsulin altered so as to have furin cleavable sites at its B-C and C-A junctions and carrying a H10D variant;

T is a human or murine TGF-α promoter;

hF is a nucleotide sequence encoding for human furin;

S is a SV40 promoter;

N is a nucleotide sequence encoding for neomycin phosphotransferase, a selectable marker gene; and SV40 polyA are polyadenylation sequences.

As seen in Table II, while no LTR sites were in the construct to serve as viral promoter/enhancers and transcription initiation sites, insulin production in HEK-293T cells grown in tissue culture medium was seen to be on the order of three times greater than that seen with the construct of Barry et al. (Human Gene Therapy 12: 131 (2001)) whether such construct was constructed to express human or murine furin.

TABLE II

| VECTOR | CONCENTRATION OF INSULIN IN MEDIUM |
| --- | --- |
| pLhI*TmFSN | 17 μIU/ml |
| pLhI*ThFSN | 12 μIU/ml |
| pcDNAChI*ThFSN | 40 μIU/ml |
| pcDNAChI*ThFSN | 59 μIU/ml |
| pcDNAChI*ThFSN | 60 μIU/ml |

Figure 5:
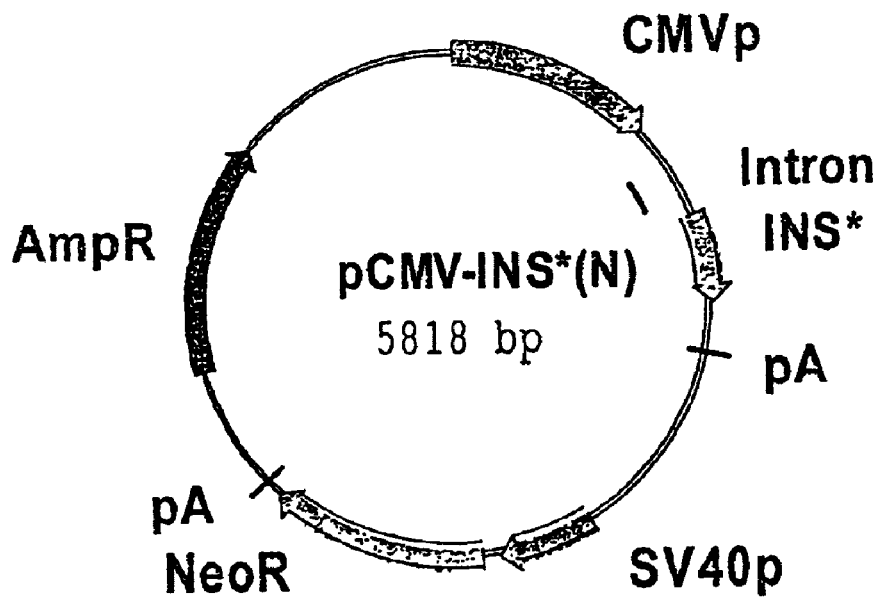
FIG. 5 illustrates a non-viral expression plasmid comprising a CMV promoter (1-750) driving constitutive expression of a nucleotide sequence encoding an altered human proinsulin (1109-1441) enhanced by poly-A at the 3' end (1630-1636), followed by Neo (2809-3603), the transcription of which is promoted by an SV40 promoter (2394-2744) and enhanced by poly-A at the 3' end (3667-3674) and a second marker unit, ampicillin (Amp) (4126-4986) with 1 intron (890-1022) (upper construct); and a non-viral expression plasmid comprising a TGF-α promoter (1-1072) driving constitutive expression of a nucleotide sequence encoding human furin (1108-3492_enhanced by poly-A at the 3' end (3692-3698), followed by hygromycin B (Hygro) (4856-5893), the transcription of which is promoted by an SV40 promoter (4456-4806) and enhanced by poly-A at the 3' end (6082-6088) and a second marker unit, ampicillin (Amp) (6708-7568) (lower construct).
Figure 5:
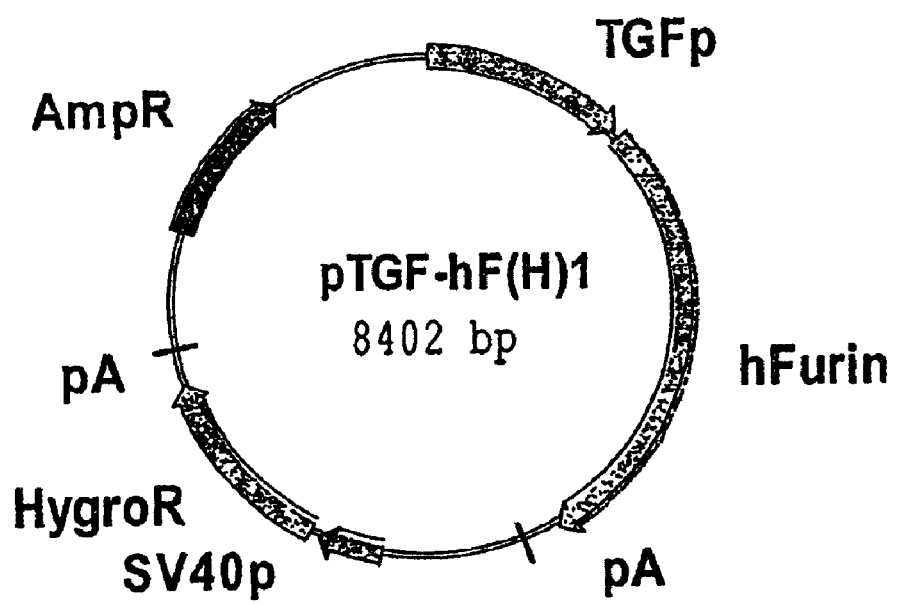

The present inventors have further designed non-viral constructs comprising a proinsulin expression cassette and non-viral constructs comprising human furin expression cassette (FIG. 5). In a proinsulin construct, the proinsulin expression cassette comprises a nucleotide sequence encoding human proinsulin altered to incorporate furin-cleavable sites at its B-C and C-A junctions, a polyadenylation site 3' to the altered human proinsulin nucleotide sequence, a promoter operably linked to the altered human proinsulin nucleotide sequence; and one or more a selectable marker expression cassettes comprising a nucleotide sequence comprising a selectable marker, and promoter of such selectable marker. In a furin construct, the human furin expression cassette comprises a nucleotide sequence encoding human furin capable of cleaving the altered sites of the proinsulin encoded by the proinsulin expression cassette, a polyadenylation site 3' to nucleotide sequence encoding the human furin, and a promoter; and one or more a selectable marker expression cassettes comprising a nucleotide sequence comprising a selectable marker, and promoter of such selectable marker. Preferably, the constructs comprise one or more polyadenylation sites.

Constructs comprising the altered proinsulin cassette may be useful in determining ability of a particular promoter in driving expression of the insulin gene. Further, construct comprising the altered proinsulin cassette or furin may be used to add copies of one or the other gene to selected cells. For example, cells can be selected for their resistance to a marker, e.g., genticin (G418), conferred by the transfection of the hI* plasmid and a different marker, e.g., hygromycin B, conferred by the transfection of the furin plasmid. The plasmids can be constructed so that the selectable marker(s) in either construct can be replaced with an alternate marker. Selectable markers include but are not limited to: genticin, hygromycin B, puromycin, zeocin, and ampicillin. Plasmids comprising the altered proinsulin cassette or furin can be transfected into cells already resistant to a different marker to generate cells that multiple copies of the hI* or furin genes.

As seen in Table III, insulin expression was driven by the following promoters: CMV, phosphoglycerate kinase (PGK), and elongation factor 1 (EF1) whereas epidermal growth factor (EGF), human insulin promoter (HIP), and phosphoenolpyruvate kinase (PEP) had little effect.

TABLE III

| VECTOR | Conc. of Insulin in medium μIU/ml U2OS, 24 h | Conc. of Insulin in medium μIU/ml U2OS, 48 h | Conc. of Insulin in medium μIU/ml HEK-293T, 24 h | Conc. of Insulin in medium μIU/ml HEK-293T, 48 h |
|---|---|---|---|---|
| pEGFP(N) | <4 | <4 | <4 | <4 |
| pCMVhI*(N) | 110 | 199 | 35 | 436 |
| pPGKhI*(N) | 111 | 198 | 28 | 366 |
| pEF1hI*(N) | 77 | 139 | 324 | 3653 |
| pHIPhI*(N) | <4 | <4 | <4 | <4 |
| pPEPhI*(N) | <4 | <4 | <4 | <4 |

EXAMPLE 1

Generation of pLhI*ThFSN

A vector comprising the murine Furin gene, pLhI*TFSN (FIG. 3) was obtained from William R. A. Osborne, The University of Washington, Seattle, Wash. Human furin cDNA was purchased from ATCC.

In pLhI*TFSN, furin-cleavable human insulin (hI*) is driven by the viral 5'LTR (L). The natural coding sequence of human insulin is altered to insert sites to be cleaved by furin and to obtain insulin that binds with higher affinity to insulin receptors (H10D variant). The altered insulin, designated as hI*, is produced constitutively as biologically inactive pro-insulin, which is processed to be active insulin by proteolytic processing by murine Furin (mF). The expression mF is dependent on glucose concentration since it is driven by glucose-responsive, TGF-alpha promoter. This vector also contains the neomycin phosphotransferase gene driven by the SV40 promoter in order to select for transduced cells.

Upon sequence of pLhI*TFSN it was noticed that there was some undefined sequence before the first initiation site (ATG) of mF. It was subsequently discovered that in this undefined sequence that there are at least two more ATG codons before the initiating ATG for furin translation. This adds more open reading frames (ORFs) that are under the control of the TGF-alpha promoter. This could potentially lead to suboptimal expression of mF. A strategy was undertaken to remove this undefined sequence and to replace mF with hF.

pLhI*TFSN was digested with BamH1 and SalI. The digest resulted in five (5) fragments as follows: 6226: pLhI*TFSN: BamHI(6021)—SalI(2013); 2406: pLhI*TFSN: BamHI(2814)—BamHI(5220); 801: pLhI*TFSN: BamHI(5220)—BamHI(6021); 778: pLhI*TFSN: SalI(2036)—BamHI(2814); 23: pLhI*TFSN: SalI(2013)—SalI(2036). The 6226 bp fragment, which contains SN, 3' LTR, the retro-viral backbone and 5'LTR and furin-cleavable human insulin was isolated. The fragment was then de-phosphorylated for use as a vector.

Human furin was PCR-amplified using human furin cDNA from ATCC as a template:

hFurin(Forward primer) (a primer containing SalI (GTC GAC) and SnaB1 (TAC GTA) restriction sites as well as Kozak sequence. CCACCATGG):

5' AAA GTC GAC TAC GTA CCA CCA TGG AGC TGA GGC CCT T 3' (SEQ ID NO:1)

hFurin (Reverse primer) (a primer containing BclI (TGA TCA) and BsiWI (CGT ACG) restriction sites)

5' AAA TGA TCA CGT ACG TCA GAG GGC GCT CTG GTC TT 3' (SEQ ID NO:2)

The product was PCR-amplified and purified, and then digested with BclI and SalI, and subcloned into the BamHI/SalI—digested 6226 fragment of pLhI*TFSN generated above, to generate a plasmid pLhI*hFSN, without the TGF-alpha promoter. This was digested with ClaI/SalI or ClaI/SnaB1, gel purified and phosphatase to be used as a recipient fragment in the next step.

The TGF-alpha promoter was PCR amplified using pLhI*TFSN as a template.

TGFp1(forward primer) (a primer containing ClaI (ATC GAT) and HpaI (GTT AAC) restriction sites):

5' AAA ATC GAT GTT AAC AGC TCC GGG TCA CTG GAG AA 3' (SEQ ID NO:3)

TGFp2(Reverse primer) (a primer containing SalI(GTC GAC) and SnaBI(TAC GTA) restriction sites):

5'AAA GTC GAC TAC GTA GGC GGA GCG GCG CCG CGG TG 3' (SEQ ID NO:4)

The product was PCR-amplified and purified, and then digested with either (ClaI and SalI) or (ClaI and SnaBI). It was then subcloned into the ClaI/SalI or ClaI/SnaB1-digested pLhI*hFSN, to generate plasmid pLhI*ThFSN (FIG. 3). The construct was generated using this strategy, sequence checked and tested for insulin production in HEK-293T cells in transient transfections. The results of transient transfections are described in Table I.

EXAMPLE 2

Generation of pLChI*ThFSN

Human mutant insulin was subcloned pcDNA 3.1 (InVitrogen) vector, in which human insulin was expressed under the cytomegalovirus (CMV) promoter (pcDNAChI*pA), the vector containing a polyA site at the 3' end. This construct, when transiently expressed in HEK-293T cells, produced much higher levels of insulin production. The vector pLhI*ThFSN was further modified to drive expression of human insulin under control of the CMV promoter as follows:

pcDNA-ChI* was digested with MfeI and EcoRV. This digest resulted in two fragments: 4642: pCDNA-ChI*: EcoRV(1312)—MfeI(162); and 1150: pCDNA-ChI*: MfeI (162)—EcoRV(1312). The 1150 bp fragment was isolated, such fragment containing the CMV promoter and human Insulin.

pLhI*ThFSN was digested with EcoRI, which resulted in two fragments as follows: 9360: pLhI*ThFSN(BI6.1.1): HpaI(2012)—EcoRI(1645); and 367: pLhI*ThFSN (BI6.1.1): EcoRI(1645)—HpaI(2012). The 9360 bp fragment was isolated, such fragment contained the entire vector excluding human insulin. This fragment was de-phosphorylated and used as a recipient fragment to clone in the 1150 bp fragment of pcDNAChI*. The construct generated using this strategy was designated as pLChI*ThFSN. The sequence was checked and tested for insulin production in HEK-293T cells in transient transfections. The results of transient transfections are described in Table I.

EXAMPLE 3

Generation of a Non-viral Vector

In order to express all three genes in a non-viral vector, each coding sequence was flanked by poly A signal at the 3' end of the coding sequence.

PCR-amplified human Furin was subcloned into pcDNA3.1 to produce pcDNAhF. Human Furin was PCR-amplified using Human furin cDNA from ATCC as template.

The primers were as follows:

hFurin(Forward primer) (the primer_contains SalI (GTC GAC) and SnaB1 (TAC GTA) restriction sites as well as Kozak sequence, CCACCATGG):

5' AAA GTC GAC TAC GTA CCA CCA TGG AGC TGA GGC CCT T 3' (SEQ ID NO:1)

hFurin (Reverse primer) (this primer contains BclI (TGA TCA) and BsiWI (CGT ACG) restriction sites):

5' AAA TGA TCA CGT ACG TCA GAG GGC GCT CTG GTC TT 3' (SEQ ID NO:2)

The PCR-amplified product was purified, and then digested with BclI and SnaBI, which was then subcloned into the BamHI/EcoRV—digested pcDNA3.1, to generate a construct pcDNAhF.

The "polyA-TGF-alpha promoter" was subcloned into pcDNAChI*. The pCMV(script)hI*ThFSN3.1 was digested with SalI, resulting in the following fragments:

7000: pCMVhI*ThF SN 3.1: SalI(2670)—SalI(1074)
1596: pCMVhI*ThF SN 3.1: SalI(1074)—SalI(2670)

The 1569 bp fragment, that included the SV40 polyA site and the TGF-alpha promoter, was isolated. pcDNAChI* was linearized with XhoI (Compatible with SalI) and the vector de-phosphorylated. The 1596 bp fragment was then subcloned into pcDNA ChI* in a non-directional cloning (i.e., the insert can go in any direction, which can be identified by restriction digests), to result in pcDNAChI*T, with a poly A site between hI* and T.

pcDNAhF from above was digested with NotI and AflII, which gave fragments as follows:

5356: pcDNAhF2: AflII(3368)—NotI(928)
2440: pcDNAhF2: NotI(928)—AflII(3368)

The 2440 bp fragment, containing the furin coding region, was isolated.

pcDNAChI*T was digested with NotI and AflII to open the vector, phosphatase the vector, and the 2440 bp furin fragment subcloned into the vector to produce pcDNAChI*ThF (FIG. 4), with poly A sites at 3' end of each hI* and hF. SN-poly present in the original vector, pcDNA3.1 is at the 3' end of hF. The vector was analyzed by restriction digests and subsequently tested in transient transfections in HEK-293T cells.

EXAMPLE

Transient Transfection of HEK-293T Cell Line

Effectene™ reagents (Qiagen Inc., Valencia, Calif.) were used to transfect the cells.

Cells were counted and adjusted to $2.5 \times 10^5$ cells/ml. Cells were plated 1.0 ml cells for $2.5 \times 10^5$ cells/60 mm dish and the volume of the media brought to 4.0 ml. Cells were allowed to adhere overnight to 40–60% confluence. Media was removed from the cells to reduce the volume to 1.5 ml in the plate. One µg DNA was added into a total of 150 µl DNA-condensation buffer (EC buffer, Qiagen Inc.) into a sterile microtube. Eight microliters of enhancer (Qiagen Inc.) was added into DNA/EC buffer, vortexed 1 sec and incubate d2–5 minutes at room temperature (RT).

Twenty-five microliters of Effectene™ was added into each tube and vortex for 10 seconds, and the tubes allowed to sit at room temperature for 5–10 min. One milliliter of media was then added, and the resulting mix pipetted up and down 2 times; the DNA mixture was added drop-wise over cells. The dish was mixed by swirling, and the cells returned to 37° C./5% $CO_2$. Complexes were removed at 4 hours, and 2.0 ml fresh media added. Cells were harvested at 24 and 48 hours, and insulin assessed in the supernatants.

As is understood by those of ordinary skill in the art, many genetically engineered cell lines do not secrete sufficient insulin to be therapeutic, or the insulin productions is not appropriately regulated. Most cell lines that have shown some degree of glucose regulated insulin production have employed a glucose responsive promoter to transcriptionally regulate the insulin gene directly. The approach of the present inventors have been to engineer cells using the vectors described above to regulate insulin production at the level of pro-insulin processing rather than at the level of insulin transcription. Cells transformed with such constructs not only secrete mature insulin, but will also produce the C-peptide that has been reported to possess vasculature and neurologic functions.

Due to the disadvantages of immunosuppression undertaken in the prior art to prevent host defense action against insulin-producing foreign cells, the present inventors have undertaken to discern human cell lines that are adapted for growth in an immunoisolation devices.

Immunoisolation devices are devices designed to be implanted in an organism which are structured to house cells in a manner to permit diffusion of nutrients and secreted therapeutic factors of the host to come into contact with the cells but that protects the cells from host immune attack. Numerous immunoisolation devices have been proposed.

U.S. Pat. No. 5,869,077 to Dionne et al. (Issue Date: Feb. 9, 1999) describes a biocompatible immunoisolatory vehicle suitable for long-term implantation into individuals comprising a core which contains a biologically moiety, such as a cell, either suspended in a liquid medium or immobilized within a hydrogel or extracellular matrix and a surrounding or peripheral region of perselective matrix or membrane which does not contain the isolated biological moiety, and which protects the biological moiety from immunological attack but has a molecular weight cutoff (advantageously 50 kD to 2000 kD) to permit passage of molecules between the patient and the core. The jacket of such device may be fabricated from materials such as polyvinylchloride, polyacrylonitrile, polymethylmethacrylate, polyvinyldifluoride, polyolefins, polysulfones and celluloses. Likewise, PCT/US99/08628 to Powers et al. teaches immunoisolation devices comprising alginate coatings, and cells seeded into semipermeable fibers. A commercially available implantable immunoisolation device is TheraCyte® (TheraCyte Inc., Irvine, Calif.). The device is designed for subcutaneous or intraperitoneal implantation and is said to enable allogeneic cell transplants without immunosuppression, and to protect xenogeneic transplants with conventional immunosuppression. The device comprises an outer vascularizing membrane of polytetrafluoroethylene (PTFE) 15 µm thick and having 5 µm pore size, and an inner, cell impermable PTFE membrane 30 µm thick and having 0.4 µm pore size. The outer membrane is said to be vascularizing, thus preventing the common problem of fibrotic encapsulation usually encountered with bioimplantable devices.

The present inventors have identified numerous human cell lines that are well adapted to in vitro culture and genetic modification, and which are adapted as well for growth in immunoisolation devices. These cells comprise but are not limited to:

TABLE IV

| CELL DESIGNATION | TISSUE TYPE | CELL DESIGNATION | TISSUE TYPE |
| --- | --- | --- | --- |
| HEPM | Palatal Mesenchyme | CRL-1486 | Fibroblast |
| U-2OS | Bone | HTB-96 | Epithelia |
| A-498 | Kidney | HTB-44 | Epithelia |
| NCI-H441 | Lung | HTB-174 | Epithelia |
| SHP-77 | Lung | CRL-2195 | Epithelia |

It is preferred that these cell lines be cultured during genetic modification according to their individual requirements as set forth by ATCC.

While the invention has been described with respect to preferred embodiments, those skilled in the art will readily appreciate that various changes and/or modifications can be made to the invention without departing from the spirit or scope of the invention as defined by the appended claims. All documents cited herein are incorporated by reference in their entirety.

What is claimed is:

1. A recombinant vector for transforming cells to produce mature human insulin, said recombinant vector comprising:
   (a) a first LTR promoter/enhancer;
   (b) a second promoter operatively linked to said first LTR promoter/enhancer; and
   (c) a nucleotide sequence encoding human proinsulin having furin cleavable sites at its B-C and C-A junctions, transcription of said human proinsulin nucleotide sequence being driven by said first LTR promoter/enhancer and said second promoter.

2. The recombinant vector of claim 1 wherein said second promoter is selected from the group consisting of: cytomegalovirus (CMV), phosphoglycerate kinase (PGK), and elongation factor 1 (EF1).

3. The recombinant vector of claim 1 wherein said nucleotide sequence encoding human proinsulin encodes a human proinsulin selected from the group consisting of: wild-type human proinsulin and human proinsulin having an H10D variant as compared to wild-type human proinsulin.

4. The recombinant vector of claim 1 further comprising:
   (a) a glucose-regulatable promoter; and
   (b) a nucleotide sequence encoding human furin, said human furin nucleotide sequence being driven by said glucose-regulatable promoter.

5. The recombinant vector of claim 4 wherein the glucose-regulatable promoter is a TGF-α promoter.

6. The recombinant vector of claim 4 further comprising:
   a constitutive promoter;
   a selectable marker gene operatively linked to said constitutive promoter; and
   a second LTR promoter/enhancer operably linked to said selectable marker gene;
   wherein said constitutive promoter and said second LTR promoter/enhancer drive the constitutive expression of said selectable marker gene.

7. The recombinant vector of claim 6 wherein said selectable marker gene is neomycin phosphotransferase.

8. The recombinant vector of claim 6 wherein said constitutive promoter is the SV40 promoter.

9. A cell transformed to produce insulin by way of the recombinant vector of claim 1.

10. A cell transformed to produce insulin by way of the recombinant vector of claim 6.

11. An expression system for inducing insulin production in a cell, said system comprising:

(a) a first expression cassette comprising:
      (1) a first LTR promoter/enhancer
      (2) a CMV promoter operatively linked to said first LTR promoter/enhancer; and
      (3) a nucleotide sequence encoding human proinsulin having furin cleavable sites at its B-C and C-A junctions, transcription of said human proinsulin nucleotide sequence being driven by said first LTR promoter/enhancer and said CMV promoter;
   (b) a second expression cassette comprising:
      (1) a glucose-regulatable promoter; and
      (2) a nucleotide sequence encoding human furin, said human furin nucleotide sequence being driven by said glucose-regulatable promoter;
   (c) a third expression cassette comprising:
      (1) a nucleotide sequence encoding a selectable marker gene; and
      (2) a constitutive promoter of said selectable marker gene operably linked to said selectable marker gene.

12. The expression system of claim 11 said nucleotide sequence encoding human proinsulin of said first expression cassette encodes a human proinsulin selected from the group consisting of: wild-type human proinsulin or human proinsulin having an H10D variant as compared to wild-type human proinsulin.

13. The expression system of claim 11 wherein said first and second expression cassettes are linked.

14. The expression system of claim 11 wherein said first and third expression cassettes are linked.

15. The expression system of claim 11 wherein said second and third expression cassettes are linked.

16. The expression system of claim 11 wherein said first, second and third expression cassettes are linked.

17. The expression system of claim 11 wherein said first and second expression cassettes are packaged in separate replicons, and wherein said first and said second expression cassettes are each linked to said third expression cassette but comprise at least different selectable marker genes of said third expression cassette.

18. The expression system of claim 11 wherein said third expression cassette further comprises a LTR promoter/enhancer.

19. The expression system of claim 11 wherein said glucose-regulatable promoter of said second expression cassette is the TGF-α promoter.

20. The expression system of claim 11 wherein said selectable marker gene of said third expression cassette is a nucleotide encoding for neomycin phosphotransferase.

21. The expression system of claim 11 wherein said constitutive promoter of said selectable marker gene of said third expression cassette is the SV40 promoter.

22. A cell transformed to produce insulin by way of the expression system of claim 11.

23. An engineered cell comprising a gene encoding for human proinsulin having furin cleavable sites at its B-C and C-A junctions and a gene encoding for fuman furin, wherein both genes are recombinant genes and the cell secretes insulin in response to glucose and wherein the cell that is transformed is selected from the group consisting of: HEPM, U-2 OS, A-498, NCI-H441, SHP-77.

* * * * *